(12) United States Patent
Lagodzki et al.

(10) Patent No.: US 9,017,365 B2
(45) Date of Patent: Apr. 28, 2015

(54) POLARIZABLE DELIVERY MECHANISM FOR MEDICAL DEVICE DEPLOYMENT

(75) Inventors: Karol Lagodzki, Bloomington, IN (US); Kathryn R. Evert, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 169 days.

(21) Appl. No.: 13/457,732

(22) Filed: Apr. 27, 2012

(65) Prior Publication Data
US 2012/0283812 A1    Nov. 8, 2012

Related U.S. Application Data

(60) Provisional application No. 61/481,466, filed on May 2, 2011.

(51) Int. Cl.
| | |
|---|---|
| *A61B 17/22* | (2006.01) |
| *A61F 2/95* | (2013.01) |
| *A61B 17/12* | (2006.01) |
| *A61M 25/10* | (2013.01) |
| *A61M 37/00* | (2006.01) |
| *A61F 2/01* | (2006.01) |
| *A61F 2/88* | (2006.01) |

(52) U.S. Cl.
CPC .............. *A61F 2/95* (2013.01); *A61M 25/1018* (2013.01); *A61M 37/0069* (2013.01); *A61M 2025/1054* (2013.01); *A61B 17/12022* (2013.01); *A61B 2017/1209* (2013.01); *A61F 2/01* (2013.01); *A61F 2/88* (2013.01); *A61F 2002/011* (2013.01); *A61F 2002/9511* (2013.01); *A61B 2017/12086* (2013.01)

(58) Field of Classification Search
CPC .............. A61B 2017/12086; A61B 2017/1209
USPC ............ 623/1.11; 606/200, 191, 194; 604/57, 604/507
See application file for complete search history.

(56) References Cited

U.S. PATENT DOCUMENTS

| | | | |
|---|---|---|---|
| 7,582,101 B2 | 9/2009 | Jones et al. | |
| 7,771,451 B2 | 8/2010 | Ramzipoor | |
| 2005/0149108 A1* | 7/2005 | Cox ............................ | 606/200 |
| 2007/0299422 A1* | 12/2007 | Inganas et al. ............... | 604/508 |
| 2012/0130418 A1* | 5/2012 | Jenson et al. ................ | 606/200 |

* cited by examiner

*Primary Examiner* — Thomas McEvoy
*Assistant Examiner* — Julie A Szpira
(74) *Attorney, Agent, or Firm* — Brinks Gilson & Lione

(57) ABSTRACT

A medical device assembly having a polarizable delivery mechanism reversibly engaged with a medical device and a method used by an operator to deploy said medical device at a targeted site in a body vessel is provided. The polarizable release mechanism generally comprises a pusher element having a distal end including at least two tines; the tines having a proximal section and a distal section, the tines being capable of exhibiting polarizable properties. The medical device has an opening sized to receive and to detachably engage the distal section of the tines. The delivery mechanism has an engaged position in which the tines securely hold the medical device and a detached position in which the tines and medical device are substantially unengaged. The operator causes the delivery mechanism to move from the engaged position to the detached position by applying or removing an energy stimulus to change the polarization.

12 Claims, 3 Drawing Sheets

POLARIZABLE DELIVERY MECHANISM FOR MEDICAL DEVICE DEPLOYMENT

CROSS-REFERENCE TO RELATED APPLICATIONS

This application claims the benefit of U.S. Provisional Application No. 61/481,466 filed on May 2, 2011, entitled "POLARIZABLE DELIVERY MECHANISM FOR MEDICAL DEVICE DEPLOYMENT" the entire contents of which are incorporated herein by reference.

FIELD

This disclosure relates generally to a mechanism for the deployment of a medical device within a patient. More specifically, this disclosure relates to a delivery assembly for a medical device and a method of mechanically releasing or detaching said device at a targeted vascular site.

BACKGROUND

A standard procedure used in the treatment of endovascular diseases is the placement of medical devices, such as embolic coils, stents, and dilation balloons, among others, at a desired or targeted site (e.g., aneurysm, etc.) within a patient. The delivery of such a medical device has typically been accomplished by a variety of means, including the use of a catheter along with a pushing wire or a means of injection, as well as a system to which the device is attached during delivery and detached once the device is proximate to the targeted site. These medical devices usually have a contracted shape that allows them to pass through the lumen of the body vessel and an expanded shape that occurs after being deployed at the targeted site.

One specific example, of such a medical device is an embolic or occlusive device that is placed within a body vessel or vasculature of the human body to filter the flow of blood through a vessel in the vasculature or to block the flow of blood within a defect in the vessel, such as an aneurysm. One example among many widely accepted types of occlusive devices is a detachable helical wire coil whose coil windings are sized to engage the wall of the vessel. Detachable coils are usually selected when the anatomy is especially distal and tortuous, a risk of coil displacement exists, or a very precise placement of the coil is required. Despite the technological advancement in the field of delivering such occlusive devices to a target site, problems still exist with many of the current means of deployment.

These problems include difficulty in positioning and repositioning the medical device before detachment from the catheter, the lack of accuracy in maneuvering the device into position at the target site, and the lengthy duration of time necessary to deploy the device. Several additional shortcomings associated with current delivery systems include the lack of control over the device once the delivery wire is out of the catheter; unreliable detachability; the inclusion of additional system assembly steps necessary to successfully detach the device; and the inclusion of a detachable mechanism that adds to the stiffness of the system creating the risk of losing delivery catheter position, to name a few.

Accordingly, there exists a desire to provide improvements in the mechanism used to detachably deploy a medical device at a targeted location in the vasculature of a patient. More particularly, there exists a desire for the continued development of a coupling mechanism that securely holds the medical device, thereby, allowing it to be effectively maneuvered throughout the deployment process, while also allowing said medical device to be easily and reliably detached once it is properly located at the target site. A mechanism that is adaptable for use with a wide variety of medical devices would be advantageous.

SUMMARY

In satisfying the above need, as well as overcoming the enumerated drawbacks and other limitations of the related art, the present disclosure generally provides a medical device assembly for use by an operator in deploying a medical device at a targeted site in a body vessel or vasculature of a patient. The medical device assembly comprises a polarizable delivery mechanism and a medical device reversibly attached thereto.

According to one aspect of the present disclosure, the polarizable delivery mechanism includes a pusher element and a medical device. The pusher element has a distal end that includes at least two tines capable of exhibiting polarizable properties. Each of the tines includes a distal section adapted to detachably engage the proximal part of the medical device. A change in the polarization exhibited by the tines induced by the application of an energy stimulus causes the tines to move toward one another, thereby, allowing the medical device to detach from the pusher element for deployment in the body vessel. The delivery mechanism may further include at least one wire in communication with the tines that is capable of providing the energy stimulus.

The polarizable delivery mechanism has an engaged position and a detached position. The distal section of the tines engages the proximal part of the medical device when the delivery mechanism is in the engaged position and disengages the proximal part of the medical device when the delivery mechanism is in the detached position. In the engaged position the tines may be either polarized or un-polarized. When polarized, the polarization of each tine is either (a) similar in nature such that the tines repel one another or (b) opposite one another with the polarization being neutralized by the application of an energy stimulus such that the tines do not attract one another.

When the tines are un-polarized in the engaged position, the tines will become polarized when the delivery mechanism is in the detached position such that the tines attract one another. However, when the tines are similarly polarized while in the engaged position so that the tines repel one another, the application of an energy stimulus in the detached position neutralizes the polarization so that the tines no longer repel one another. Finally, when the tines are oppositely polarized while in the engaged position with such polarization being neutralized by the application of an energy stimulus, the energy stimulus is removed in the detached position so that the tines are now allowed to attract one another.

According to another aspect of the present disclosure, the tines are magnetically polarizable. The tines may be at least partially made from a ferromagnetic metal, a ferromagnetic metal alloy, a permanent magnet, or mixture or combination thereof.

According to yet another aspect of the present disclosure, a method for use by an operator in deploying a medical device at a targeted site in a body vessel is provided. The method generally comprises the steps of introducing a catheter having a distal end and a proximal end into a body vessel, placing a medical device assembly as described herein that includes a polarizable delivery mechanism and a medical device into the proximal end of the catheter, moving the medical device assembly in an engaged position through the catheter to a targeted site in the body vessel, causing the polarizable delivery mechanism to from the engaged position to a detached position, and deploying the medical device at the targeted site in the vessel.

Through the use of this method, the operator can either apply an energy stimulus to the tines or remove an energy stimulus already applied to the tines in order to alter the polarization exhibited by the tines, thereby allowing the tines to move toward one another in order to detach the medical device. This method also provides the operator the opportunity to position the medical device proximate to the targeted site after the device exits the distal end of the catheter and prior to causing the polarizable delivery mechanism to move from the engaged position to the detached position.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. One skilled-in-the-art will understand that a helical coil is used in the Figures as an example of a medical device and that other medical devices may be utilized without exceeding the scope of the disclosure.

DETAILED DESCRIPTION

Figure 1A:
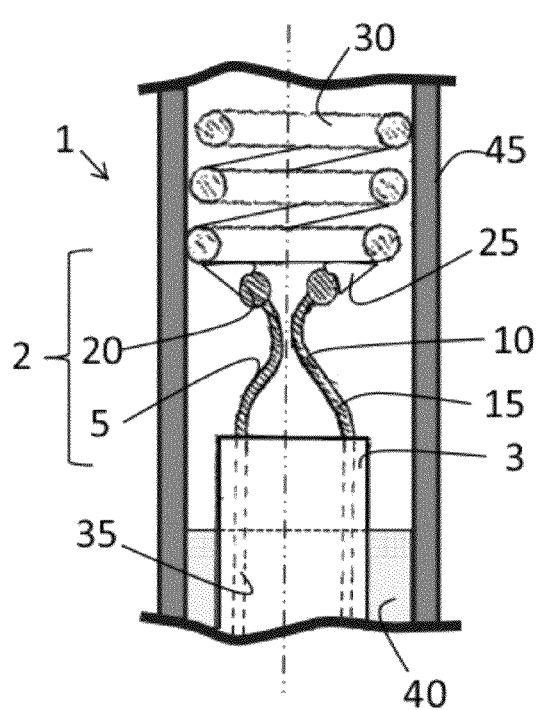
FIG. 1A is a perspective view of a polarizable delivery mechanism in an engaged position prepared according to the teachings of the present disclosure.

The following description is merely exemplary in nature and is in no way intended to limit the present disclosure or its application or uses. It should be understood that throughout the description and drawings, corresponding reference numerals indicate like or corresponding parts and features.

The present disclosure generally provides a medical device assembly that includes a polarizable delivery mechanism for the deployment of a medical device at a targeted site in a body vessel or vasculature of a patient, as well as a method of using said delivery mechanism. The polarizable delivery mechanism basically comprises a pusher element, such as a guide wire, having a proximal end and a distal end. The distal end of the pusher element has two tines adapted to reversibly interact with a medical device to either hold or release said device in an engaged or detached position, respectively. The polarizable delivery mechanism has an engaged position in which the tines make contact with the inner wall of an opening in the medical device to securely hold the device during deployment. The opening in the medical device may be part of a bracket or other feature on the medical device designed to interact with the tines of the pusher element. The medical device may be attached proximate to the distal end of the pusher element during the manufacturing process or by the attending operator prior to performing the deployment procedure by placing the tines of the distal section of the pusher element into the opening in the medical device such that the medical device is releasably held by the polarizable delivery mechanism.

In use, the pusher element, with the medical device attached, is advanced through a catheter to a targeted vascular site in a patient. Upon exiting the distal end of the catheter, the polarizable delivery mechanism is made to undergo a transition from an engaged position to a detached position, in which the tines of the pusher element no longer engage the medical device, thereby, allowing the medical device to be released and/or deployed. The pusher element can then be withdrawn, leaving the medical device in the desired position. Thus, the polarizable delivery mechanism of the present disclosure does not automatically release the medical device when it is extruded from the catheter, but rather, requires the action of the operator to initiate the mechanism to switch from the coupled or engaged position to its detached or unengaged position.

Referring to FIG. 1A, the medical device assembly 1 includes a polarizable delivery mechanism 2 that comprises a pusher element 3 defined by a proximal and distal end with at least two tines 5, 10 located at the distal end. Each of the tines 5, 10 also are defined by a proximal 15 and a distal 20 section. The proximal section 15 is in contact with the distal end of the pusher element 3, while the distal section 20 of the tines is capable of interacting with a bracket or other mechanism 25 located on the proximal part of a medical device 30. The tines 5, 10 may be made of a material that can become polarized when appropriately activated. The tines 5, 10 may become activated via the application of an energy stimulus traveling either through the pusher element 3 or through wires 35 incorporated into the pusher element 3 for that specific purpose. One skilled-in-the-art will understand that two tines 5, 10 are shown in the Figures as one example of the polarizable delivery mechanism 2 and that more than two tines 5, 10 may be used without exceeding the scope of the present disclosure.

Still referring to FIG. 1A, according to one aspect of the present disclosure, the tines 5, 10 are positioned to interact with the bracket 25 of the medical device 30 in an inactive state. This inactive state may include the tines 5, 10 not being polarized or in the case of tines 5, 10 being used that are permanently polarized, the tines 5, 10 can be subjected to an induced field that cancels the corresponding field exerted by the polarized tines 5, 10. The induced field may be established by applying an energy stimulus through wires 35 incorporated into the pusher element 3 that are in communication with the tines 5, 10. In the case where the energy stimulus is a magnetic field, the magnetic field can be generated by applying an electric current to an electric coil arrangement (not shown) located somewhere along the path of the wires 35, even at the proximal end of the wires 35 located outside the body vessel or vasculature 45 of the patient. The pusher element 3 with the polarizable delivery mechanism 2 in its engage position pushes the medical device 30 through a catheter 40 positioned within the vasculature 45 of a patient. The medical device 30 in contact with the tines 5, 10 of the pusher element 3 exits the end of the catheter 40. Once located at the targeted site in the vasculature 45, the medical device 30 may be detached from the pusher element 3 as shown in FIG. 1B.

Figure 1B:
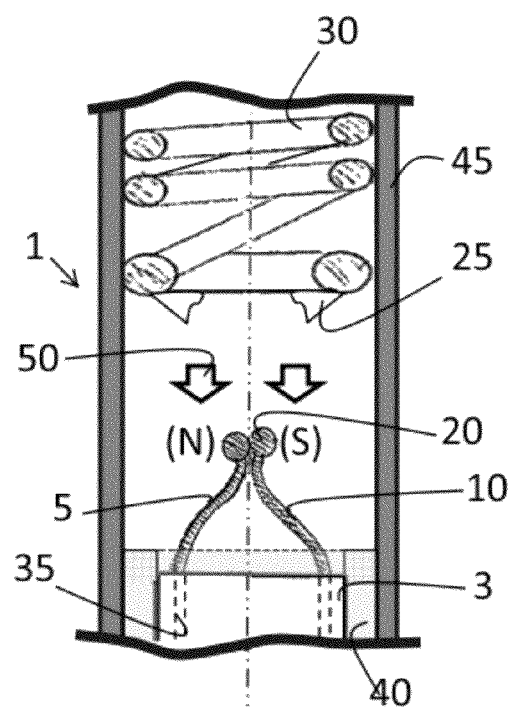
FIG. 1B is a perspective view of the polarizable delivery mechanism of FIG. 1A shown in a detached position according to another aspect the present disclosure.

Referring now to FIG. 1B, the medical device 30 is detached from the tines 5, 10. When the tines 5, 10 are un-polarized in the engaged position, these tines 5, 10 become polarized in the detached position such that each tine 5, 10 represents an opposite charge or magnetic pole as illustrated in FIG. 1B as a north pole (N) and a south pole (S). The polarization of the tines 5, 10 may occur by the application of an energy stimulus that induces the polarization of the tines 5, 10 or in the case where the tines 5, 10 are permanently polarized, by removing the energy stimulus that is being used to neutralize the attraction between the tines 5, 10. Once oppositely polarized, the tines 5, 10 attract one another, thereby, moving towards one another and losing contact with the bracket 25 of the medical device 30. The lack of contact between the tines 5, 10 and the bracket 25 allows the medical device 30 to become detached from the pusher element 3. Upon becoming detached from the medical device 30, the pusher element 3 may be withdrawn 50 from the vasculature 45 of the patient.

In order to demonstrate the polarization of the tines 5, 10, the mechanism of polarization is described in FIGS. 1A, 1B, 2A, and 2B as being magnetic in nature. However, one skilled in the art will understand that other polarization mechanisms may be used without exceeding the scope of the present disclosure, provided such polarization mechanisms are capable of causing the tines 5, 10 to move relative to one another in order to attach to or detach from a medical device 30.

Figure 2A:
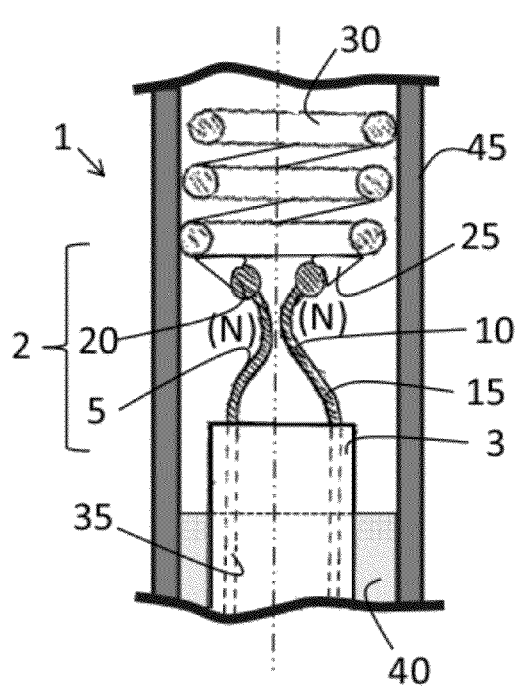
FIG. 2A is another perspective view of a polarizable delivery mechanism in an engaged position prepared according to the teachings of the present disclosure.

Referring now to FIG. 2A, another aspect of the medical device assembly 1 of the present disclosure is shown. According to this aspect of the present disclosure, the polarizable delivery mechanism 2 comprises a pusher element 3 defined by a proximal and distal end with two tines 5, 10 located at the distal end. Each of the tines 5, 10 also are defined by a proximal 15 and a distal 20 section. The proximal section 15 is in contact with the distal end of the pusher element 3, while the distal section 20 of the tines is capable of interacting with a bracket or other mechanism 25 located on the proximal end of a medical device 30. The tines 5, 10 are made of a material that can become polarized when appropriately activated. The tines 5, 10 may become activated via the application of an energy stimulus traveling either through the pusher element 3 or through wires 35 incorporated into the pusher element 3 for that specific purpose.

Still referring to FIG. 2A, the tines 5, 10 are positioned to interact with the bracket 25 of the medical device 30 in an active state. This active state includes the tines 5, 10 being polarized. More specifically, the tines 5, 10 are either permanently magnetized by the inclusion of a magnet in whole or in part or are polarized by the application of an induced field. The tines 5, 10 are polarized such that the tines 5, 10 exhibit the same charge or magnetic pole as illustrated in FIG. 2A as a north pole (N). In this case, the tines 5, 10 repel one another, thereby, causing the tines 5, 10 to engage the bracket 25 of the medical device.

The induced field may be established by applying an energy stimulus through wires 35 incorporated into the pusher element 3 that are in communication with the tines 5, 10. The energy stimulus or magnetic field can be generated by applying an electric current to an electric coil arrangement (not shown) located somewhere along the path of the wires 35, even at the proximal end of the wires 35 located outside the body vessel or vasculature 45 of the patient. The pusher element 3 with the polarizable delivery mechanism 2 in its engaged position pushes the medical device 30 through a catheter 40 positioned within the vasculature 45 of a patient. The medical device 30 in contact with the tines 5, 10 of the pusher element 3 exits the end of the catheter 40. Once located at the targeted site in the vasculature 45, the medical device 30 may be detached from the pusher element 3 as shown in FIG. 2B.

Figure 2B:
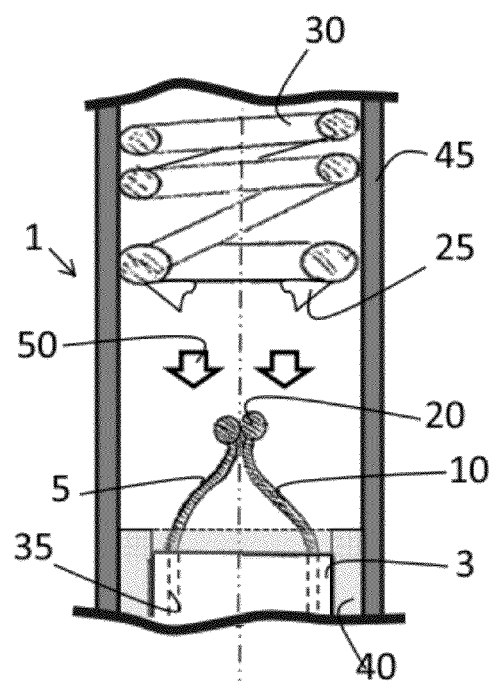
FIG. 2B is a perspective view of the polarizable delivery mechanism of FIG. 2A shown in a detached position according to another aspect of the present disclosure.

Referring now to FIG. 2B, the medical device 30 is detached from the tines 5, 10 upon the tines 5, 10 becoming un-polarized. The tines 5, 10 may become un-polarized by removing the induced field or in the case of permanent magnets being present in the tines 5, 10, inducing a magnetic field capable of opposing and cancelling the field exhibited by the magnets via the application of a stimulus through the wires 35 attached to the tines 5, 10. Once the tines 5, 10 are no longer polarized, the tines 5, 10 will no longer repel one another, thereby, allowing the tines 5, 10 to relax and move towards one another. This movement towards one another will cause the tines 5, 10 to disengage from contact with the bracket 25 of the medical device 30. The lack of contact between the tines 5, 10 and the bracket 25 allows the medical device 30 to become detached from the pusher element 3. Upon becoming detached from the medical device 30, the pusher element 3 may be withdrawn 50 from the vasculature 45 of the patient.

The polarizable delivery mechanism 2 of the medical device assembly 1 has two positions relative to the medical device 30. These positions are, namely, an engaged position and a detached position. In the engaged position, the tines 5, 10 of polarizable delivery mechanism 2 engage the bracket 25 of the medical device 30 and allows the pusher element 3 to move the polarizable delivery mechanism 2 and medical device 30 together as a medical device assembly 1, even after the medical device 30 is extruded from the end of the delivery catheter 40. In the detached position, the polarizable delivery mechanism 2 does not engage the medical device 30 and the medical device 30 is released or deployed at the selected target site in the vasculature 45 of the patient.

The medical device assembly 1 is designed such that the default position for the polarizable delivery mechanism 2 is the engaged position. The switching between the engaged and detached positions is controlled by an operator, such as a physician or surgeon, through the application of an energy stimulus, such as an electric charge to a coil or other means to induce the polarization of the tines 5, 10.

The tines 5, 10 may be made of any material that can be polarized such that movement of the tines 5, 10 can thereby be induced. Several examples of materials that can be magnetically polarized include, but are not limited to, ferromagnetic metals and metal alloys comprising iron (Fe), nickel (Ni), cobalt (Co), gadolinium (Gd), and mixtures or combinations thereof. The tines 5, 10 may also comprise in whole or in part a magnetic material, such as an Alnico magnet; a rare earth magnet; such as those described as a Neodymium (NdFeB) magnets or samarium cobalt (SmCo) magnets; a ceramic magnet, such as a strontium ferrite magnet; or a combination or mixture thereof, among others.

The ends of the tines 5, 10 in the distal section 20 of each tine 5, 10 are represented in FIGS. 1A-2B as circular balls. However, one skilled in the art will understand that these ends can be any shape capable of reversibly engaging the bracket 25 of the medical device 30 without exceeding the scope of the present disclosure. Similarly, the bracket 25 on the proximal part of the medical device 30 may be any shape known to one skilled in the art capable of reversibly engaging the tines 5, 10 of the polarizable delivery mechanism 2.

The polarizable delivery mechanism 2 as described herein can be adapted to be used with a variety of medical devices 30, including, but not limited to, embolic protection devices, occlusive devices, stents, and dilation balloons, among others. The medical device 30 may comprise any structure known to one skilled-in-the-art, including for example, occlusive devices of tubular structures, having braids, coils, a combination of braids and coils, or the like. The occlusive device may change shape during deployment, such as changing from a collapsed configuration to an expanded configuration. One example, among many examples, of a medical device 30 used with the polarizable delivery mechanism 2 to form the medical device assembly 1 of the present disclosure is a Nester® embolization coil (Cook Medical Incorporated, Bloomington, Ind.).

The delivery catheter 40 used to deliver the medical device 30 may be made of any material known to one skilled-in-the-art. Such material may include but not be limited a polyimide, polyether amide, nylon, polytetrafluoroethylene (PTFE), polyetheretherketone (PEEK), and mixtures or copolymers thereof. In its basic form, the catheter is a hollow elongated tube sized to receive the medical device 30 attached to the polarizable delivery mechanism 2. The length of the delivery catheter 40 may be any length necessary or desired to deploy the medical device 30 at the targeted site in the body vessel or vasculature 45 of a patient.

Another objective of the present disclosure is to provide a method of deploying a medical device 30 at a targeted site in the vasculature of a patient. This method generally comprises the steps of introducing the medical device assembly 1 described herein into the vasculature 45 of the patient, wherein the polarizable delivery mechanism 2 of the medical device assembly 1 is in its engaged position with the medical device 30; and then switching the polarizable delivery mechanism 2 to its detached position, thereby, deploying the medical device 30 at the targeted or desired site.

Figure 3:
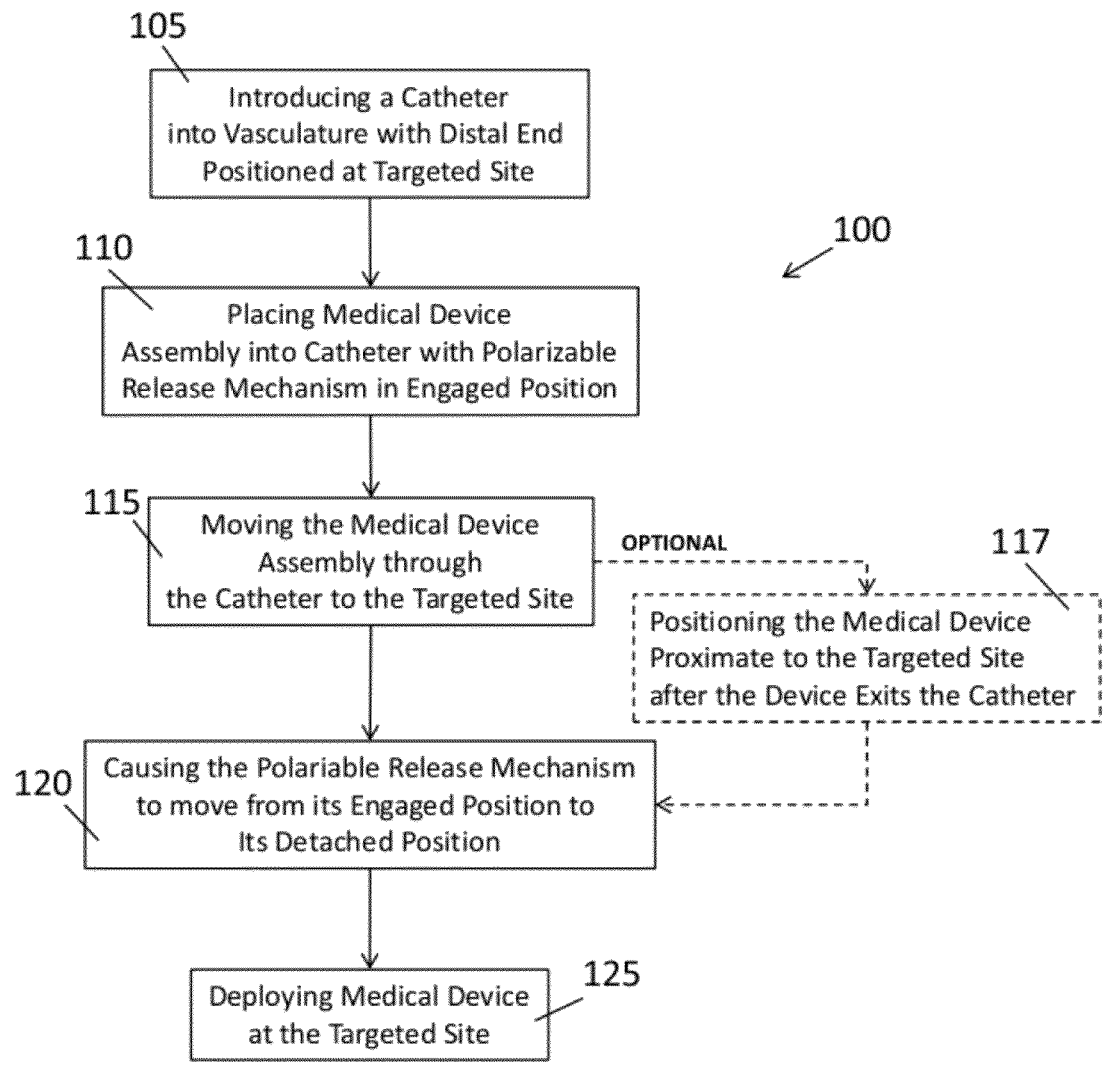
FIG. 3 is a schematic representation of a method of deploying a medical device into a vasculature of a patient using a medical device assembly having polarizable delivery mechanism made according to the teachings of the present disclosure.

FIG. 3 depicts an example of a method 100 used to deploy a medical device 30 to a targeted or desired site in the vasculature 45 of a patient. This method 100 generally comprises introducing 105 a catheter 40 into the vasculature 45 of a patient and positioning the distal end of said catheter 40 at a desired or targeted site. A medical device assembly 1 including the aforementioned medical device 30 and polarizable delivery mechanism 2 is then placed 110 into the catheter 40. At this time, the polarizable delivery mechanism 2 is in its engaged position and securely holds the medical device 30. The pusher element 3 is then allowed to move 115 the medical device assembly 1 through the catheter 40 to the targeted site. Optionally, the operator may further position 117 the medical device 30 proximate to the targeted site after the device 30 exits the catheter 40. The operator then causes the polarizable delivery mechanism 2 to move 120 from its engaged position to its detached position. The polarizable delivery mechanism 2 transitions from the engaged position to the detached position through the application or removal of an energy stimulus. This operator action causes the tines 5, 10 to move such that contact between the tines 5, 10 and the medical device 30 is reduced, thereby, allowing the medical device 30 to be deployed 125 into the vessel or vasculature 45 of the patient at the targeted site.

The present disclosure provides a polarizable delivery mechanism 3 that securely holds a medical device 30 during the deployment of the medical device 30. The polarizable delivery mechanism 2 also allows for the easy and reliable detachment of the medical device 30 once the device 30 is properly positioned proximate to the targeted site. The polarizable delivery mechanism 2 of the present disclosure provides the operator (e.g., interventionalist, etc.)) with improved control over the medical device 30 during its deployment, and allows the operator to position and even reposition the medical device 30 at the targeted site in the vasculature 45 of a patient before detachment. One skilled in the art will understand that the polarizable delivery mechanism 2 of the present disclosure is readily adaptable for use with a wide variety of medical devices 30.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A medical device assembly having a polarizable delivery mechanism for use by an operator in deploying a medical device at a targeted site in a body vessel, the medical device assembly comprising:
    a delivery mechanism including a pusher element having a proximal end and a distal end, the distal end including at least two tines; the tines having a proximal section and an distal section, the tines capable of exhibiting polarizable properties; and
    a medical device having a proximal part and a distal part; the proximal part adapted to detachably engage the distal section of the tines, the tines being separated from each other defining a default position for engaging the proximal part of the medical device, the default position being unactivated by an energy stimulus, the tines being adapted to be selectively engaged and disengaged;
    wherein a change in the polarization exhibited by the tines causes the tines to move toward one another, thereby, allowing the medical device to detach from the pusher element for deployment in the body vessel.

2. The medical device assembly of claim 1, wherein the polarizable delivery mechanism has an engaged position and a detached position; the distal section of the tines engaging the proximal part of the medical device when in the engaged position and disengaging the proximal part of the medical device when in the detached position.

3. The medical device assembly of claim 2, wherein the delivery mechanism further includes at least one wire in communication with the tines, the wire capable of providing an energy stimulus that can alter the polarization exhibited by the tines.

4. The medical device assembly of claim 3, wherein in the engaged position the tines exhibit one selected from the group of being polarized or not being polarized.

5. The medical device assembly of claim 4, wherein the polarization of the tines is similar such that the tines repel one another or the polarization of each tine is opposite one another with such polarization being neutralized by the application of an energy stimulus such that the tines do not attract one another.

6. The medical device assembly of claim 4, wherein when the tines are not polarized in the engaged position, the tines becoming polarized in the detached position such that the tines attract one another.

7. The medical device of claim 5, wherein when the tines are polarized in the engaged position such that the tines repel one another, the application of an energy stimulus neutralizes the polarization of the tines in the detached position such that the tines no longer repel one another.

8. The medical device of claim 5, wherein when the tines are oppositely polarized in the engaged position with such polarization being neutralized by the application of an energy stimulus, the energy stimulus is removed in the detached position, such that the tines are allowed to attract one another.

9. The medical device of claim 1, wherein the tines are magnetically polarizable.

10. The medical device assembly of claim 9, wherein the tines are at least partially made from a ferromagnetic metal, a ferromagnetic metal alloy, a permanent magnet, or mixture or combination thereof.

11. The medical device of claim 1, wherein the medical device is one selected from the group of embolic protection devices, occlusive devices, stents, and dilation balloons.

12. A medical device assembly having a polarizable delivery mechanism for use by an operator in deploying a medical device at a targeted site in a body vessel, the medical device assembly comprising:

a delivery mechanism including a pusher element having a proximal end and a distal end, the distal end including at least two tines; the tines having a proximal section and an distal section, the tines capable of exhibiting polarizable properties; and a medical device having a proximal part and a distal part; the proximal part adapted to detachably engage the distal section of the tines, the tines being separated from each other defining a default position for engaging the proximal part of the medical device, the default position being unactivated by an energy stimulus, each proximal section extending distally from the distal end and being out of contact with any other proximal section in the default position;

wherein a change in the polarization exhibited by the tines causes the tines to move toward one another, thereby, allowing the medical device to detach from the pusher element for deployment in the body vessel.

\* \* \* \* \*